United States Patent
Aso et al.

(10) Patent No.: US 6,204,409 B1
(45) Date of Patent: Mar. 20, 2001

(54) URETHANE COMPOUND AND PROCESS FOR PRODUCING POLYCYCLIC ALIPHATIC DIISOCYANATE

(75) Inventors: Shinji Aso; Takeshi Noguchi; Shinji Ogawa, all of Kanagawa (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/424,058

(22) PCT Filed: Mar. 30, 1999

(86) PCT No.: PCT/JP99/01620

§ 371 Date: Nov. 18, 1999

§ 102(e) Date: Nov. 18, 1999

(87) PCT Pub. No.: WO99/50234

PCT Pub. Date: Oct. 7, 1999

(30) Foreign Application Priority Data

Mar. 31, 1998 (JP) .................................................. 10-087227

(51) Int. Cl.$^7$ ................................................. C07C 271/20
(52) U.S. Cl. ............................................................. 560/115
(58) Field of Search ............................................. 560/115

(56) References Cited

FOREIGN PATENT DOCUMENTS

| | | |
|---|---|---|
| 1 923 398 | 11/1970 | (DE) . |
| 0 491 357 | 6/1992 | (EP) . |
| 51-138660 | 11/1976 | (JP) . |
| 55-120551 | 9/1980 | (JP) . |
| 57-82360 | 5/1982 | (JP) . |
| 59-172451 | 9/1984 | (JP) . |
| 2-108657 | 4/1990 | (JP) . |
| 4-222878 | 8/1992 | (JP) . |
| 6-41045 | 2/1994 | (JP) . |
| 6-157451 | 6/1994 | (JP) . |
| 6-172292 | 6/1994 | (JP) . |
| 8-277255 | 10/1996 | (JP) . |
| 10-7641 | 1/1998 | (JP) . |

*Primary Examiner*—Gary Geist
*Assistant Examiner*—Taylor V. Oh
(74) *Attorney, Agent, or Firm*—Burns, Doane, Swecker, & Mathis, L.L.P.

(57) ABSTRACT

A novel urethane compound utilized as a raw material of block isocyanate, diisocyanate, developing agent for thermosensible paper, powder paint and the like is provided, and it is a biscarbamate represented by the following general formula (1):

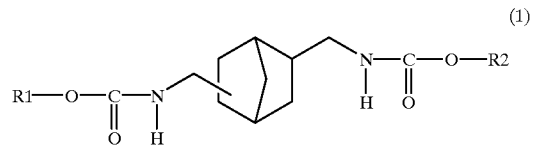

(wherein, R1 and R2 may be the same or different and represent a straight or branched alkyl group, (substituted) cycloalkyl group or (substituted) aryl group.). Further disclosed is a method for producing a polycyclic aliphatic diisocyanate by thermally-decomposing a biscarbamate represented by the general formula (1).

10 Claims, 8 Drawing Sheets

URETHANE COMPOUND AND PROCESS FOR PRODUCING POLYCYCLIC ALIPHATIC DIISOCYANATE

TECHNICAL FIELD

The present invention relates to a novel urethane compound. More particularly, the present invention relates to a novel biscarbamate compound having a norbornane skeleton.

Further, the present invention relates to a method for producing a polycyclic aliphatic diisocyanate using the above-described urethane compound, and more particularly, a method for producing a polycyclic aliphatic diisocyanate having a norbornane skeleton.

BACKGROUND ART

Conventionally, aromatic urethane and (cyclic)aliphatic urethane are known as urethane compounds, and typical examples thereof include methyl carbamate, ethyl carbamate, diethyltolylene-2,4-dicarbamate, dimethylmetaxylylene dicarbamate, 1,4-bis(methoxycarbonylaminomethyl)cyclohexane, di-n-butylhexamethylene-1,6-dicarbamate, 5-(butoxycarbonylamino)-1-(butoxycarbonylaminomethyl)-1,3,3-trimethylcyclohexane and the like, and they are utilized in various uses.

Further, though developing agents for thermosensible paper, powder paints (e.g., electrodeposition paint and the like), spectacle lenses and the like obtained by using as a raw material a diisocyanate compound having a norbornane skeleton have excellent properties, as their production method, there is only known a method in which carbamoyl obtained by reaction of a diamine compound having a norbornane skeleton with phosgene is thermally-decomposed. However, phosgene has strong toxicity, and in addition, phosgene and hydrochloric acid by-produced in large amount require complicated treatment and an apparatus for the treatment should have corrosion. resistance leading to complicated constitution.

DISCLOSURE OF THE INVENTION

An object of the present invention is to provide a novel urethane compound which can be utilized as a raw material of block isocyanate, diisocyanate, developing agent for thermosensible paper, powder paint and the like. Another object of the present invention is to provide a production method thereof, and a method for producing a cyclic aliphatic diisocanate by using a biscarbamate compound having a norbornane skeleton which is a novel urethane compound, without using phosgene.

The present inventors have widely studied for attaining the above-described object, and as a result, found that a urethane compound having specific structure is novel and is a useful compound for the above-described uses, thus completed the present invention.

Namely, an object of the present invention is to provide a novel urethane compound represented by the following general formula (1):

(wherein, R1 and R2 may be the same or different and represent a straight or branched alkyl group, (substituted) cycloalkyl group or (substituted) aryl group.).

The present inventors have found that a diisocyanate compound having a norbornane skeleton can be produced by using a biscarbamate compound having a norbornane skeleton without using phosgene, thus completed the present invention.

Namely, the present invention provides the following subjects (1), (2) and (3) to (10).

(1) A biscarbamate represented by the following general formula (1):

(wherein, R1 and R2 may be the same or different and represent a straight or branched alkyl group, (substituted) cycloalkyl group or (substituted) aryl group.).

(2) A novel urethane compound comprising a biscarbamate described in (1) above.

(3) A method for producing a biscarbamate compound wherein a biscarbamate compound described in (1) above is produced from urea or carbonate.

(4) A method for producing a biscarbamate compound wherein in producing a biscarbamate compound described in (1) above using a diamine compound, urea and aliphatic alcohol, the production is conducted while removing out of the reaction system ammonia by-produced in reaction of the diamine compound, urea and aliphatic alcohol.

(5) The method for producing a biscarbamate compound according to (4) described above, wherein vapor phase is drawn out from a reaction vessel and is condensed, then, a condensed component is recycled to the reaction vessel, and a non-condensed component is also recycled to the reaction vessel after removal of ammonia therefrom.

(6) The method for producing a biscarbamate compound according to (4) described above, wherein the production is conducted while maintaining the ammonia concentration in the reaction solution at 1 wt. % or less.

(7) A method for producing a polycyclic aliphatic diisocyanate wherein a cyclic diisocyanate is produced by thermally-decomposing a biscarbamate described in (1) above.

(8) The method for producing a polycyclic aliphatic diisocyanate according to (7) described above, wherein the thermal-decomposition is conducted at a total content of compounds having a norbornane ring in the thermal-decomposition reaction solution of 60 wt. % or more and a content of a biscarbamate in the thermal-decomposition reaction solution of 50 wt. % or less.

(9) The method for producing a polycyclic aliphatic diisocyanate according to (7) described above, wherein a biscarbamate is thermally-decomposed, the thermally-decomposed product is separated into a mixture in which the total content of compounds having a norbornane ring is 60 wt. % or more and the content of a biscarbamate is 50 wt. % or less, and other components, and the mixture is thermally-decomposed to produce a polycyclic aliphatic diisocyanate.

(10) The method for producing a polycyclic aliphatic diisocyanate according to (7) described above, wherein the thermal-decomposition reaction is conducted at least at two stages, and thermal-decomposition of the latter stage is conducted at a temperature at least 5° C. higher than that of thermal-decomposition of the former stage.

BEST MODES FOR CARRYING OUT THE INVENTION

The present invention will be illustrated below further in detail.

Biscarbamate compound

The novel urethane compound in the present invention is, more specifically, a compound containing a novel biscarbamate compound.

In the present invention, the novel biscarbamate compound is a compound having structure represented by the following general formula (1):

(1)

(wherein, R1 and R2 may be the same or different and represent a straight or branched alkyl group, (substituted) cycloalkyl group or (substituted) aryl group.).

Specific examples of the straight or branched alkyl group in the general formula (1) above include a methyl group, ethyl group, n-propyl group, ispropyl group, n-butyl group, sec-butyl group, tert-butyl group, various pentyl groups, hexyl groups, heptyl groups, octyl groups, nonyl groups, decyl groups and the like.

As the (substituted) cycloalkyl group, various alkyl groups are listed such as a cyclopentyl group, methylcyclopentyl group, cyclohexyl group, methylcyclohexyl group, ethylcyclohexyl group, cyclooctyl group, cyclohexylethyl group, benzyl group, phenetyl group, phenylbutyl group and the like.

Further, as the (substituted) aryl group, various phenyl groups are listed such as a phenyl group, xylyl group, naphthyl group, ethylphenyl group, propylphenyl group and the like.

Production method of biscarbamate

The method for producing a urethane compound according to the present invention is not particularly restricted, and there are various known methods for the production as listed below.

<1> A method in which a urethane compound is synthesized by reaction of urea or N-unsubstituted carbamate and an aliphatic alcohol or aromatic hydroxy compound with amine compound.

<2> A method in which a urethane compound is synthesized by oxidative carbonylation in which an amine compound is reacted with carbon monooxide and molecule oxygen or nitro compound in the presence of an aliphatic alcohol or aromatic hydroxy compound.

<3> A method in which a urethane compound is produced by reaction of an amine compound with a carbonate.

<4> A method in which a urethane compound is synthesized by transesterification of an aliphatic alcohol or aromatic hydroxy compound with a N-substituted β-hydroxyalkyl carbamate obtained by reaction of an amine compound with an alkylene carbonate.

<5> A method in which a urethane compound is produced by reaction of an isocyanate compound with a (cyclic) aliphatic alcohol or aromatic hydroxy compound.

The above-descried production methods will be explained below more specifically.

<1> Regarding the method in which a urethane compound is synthesized by reaction of urea or N-unsubstituted carbamate and an aliphatic alcohol or aromatic hydroxy compound with amine compound, as disclosed in Japanese Patent Application Laid-Open (JP-A) Nos. 8-277255 and 6-41045 and the like, the reaction is conducted while removing by distillation ammonia by-produced at a emperature of 100 to 280° C. in the presence of an excess liphatic alcohol or aromatic hydroxy compound to obtain urethane compound of the present invention.

<2> Regarding the method in which a urethane compound is synthesized by oxidative carbonylation in which an amine compound is reacted with carbon monooxide and molecule oxygen or nitro compound in the presence of an aliphatic alcohol or aromatic hydroxy compound, as disclosed in JP-A Nos. 55-120551 and 59-172451 and the like, the reaction is conducted under conditions of a temperature of 130 to 250° C. and a pressure of 3 to 30 MPa using as a catalyst a platinum group metal (compound such as palladium, rhodium and the like to obtain a urethane compound of the present invention.

<3> Regarding the method in which a urethane compound is produced by reaction of an amine compound with a carbonate, as disclosed in JP-A Nos. 10-7641 and 6-172292 and the like, the reaction is conducted at a temperature of 30 to 160° C. or so under normal pressure or under increased pressure using as a catalyst an alkaline (earth) metal alkoxide, basic ion-exchange resin or the like to obtain a urethane compound of the present invention.

<4> Regarding the method in which a urethane compound is synthesized by transesterification of an aliphatic alcohol or aromatic hydroxy compound with a N-substituted β-hydroxyalkyl carbamate obtained by reaction of an amine compound with an alkylene carbonate, as disclosed in JP-A No. 57-82360 and the like, an amine compound is reacted with an alkylene carbonate at a temperature of 70 to 100° C. to obtain a N-substituted β-hydroxyalkyl carbamate and the reaction is conducted while removing a glycol by-produced at a temperature of 100 to 140° C. under reduced pressure using as a catalyst tin (compound) or thallium (compound) to obtain a urethane compound of the present invention.

<5> The method in which a urethane compound is produced by reaction of an isocyanate compound with a (cyclic) aliphatic alcohol or aromatic hydroxy compound is publicknown, and the reaction thereof is disclosed in Kirk-Othmer: Encyclopedia of Chemical Technology, Third Edition, 13 p.789 and the like.

Any of these methods may be used for the production, and when a biscarbamate compound having norbornane skeleton which is a novel urethane compound is utilized as a raw material for producing a polycyclic aliphatic diisocyanate, the method <1> or <3> is preferable from the standpoint of easy availability of raw materials thereof.

Raw material of biscarbamate

Raw materials used in the above-described methods <1> to <5> for obtaining a urethane compound of the present invention will be described below.

Amine compound

Specific examples of the amine compound which is a raw material of a urethane compound represented by the general formula (1) include 2,5-bis(aminomethyl)bicyclo[2,2,1] heptane or 2,6-bis(aminomethyl)bicyclo[2,2,1] heptane or mixtures thereof.

Aliphatic and alicyclic alcohol and aromatic hydroxy compound

Specific examples of the aliphatic alcohol which is a raw material of a urethane compound represented by the general formula (1) include various alcohols such as methyl alcohol, ethyl alcohol, n-propyl alcohol, isopropyl alcohol, n-butyl alcohol, sec-butyl alcohol, tert-butyl alcohol, pentyl alcohol, hexyl alcohol, heptyl alcohol, octyl alcohol, nonyl alcohol, decyl alcohol and the like.

Examples of the cyclic aliphatic alcohol include various alcohols such as cyclopentyl alcohol, metylcyclopentyl alcohol, cyclohexyl alcohol, methylcyclohexyl alcohol, ethylcyclohexyl alcohol, cyclooctyl alcohol, cyclohexylethyl alcohol, benzyl alcohol, phenetyl alcohol, phenylbutyl alcohol and the like.

Specific examples of the aromatic hydroxy compound include various hydroxy compounds such as phenol, xylenol, naphthol, ethylphenol, propylphenol and the like.

Carbonate

Specific examples of the carbonate which is a raw material of a urethane compound represented by the general formula (1) include various carbonates such as dimethyl carbonate, diethyl carbonate, diphenyl carbonate and the like.

Alkylene carbonate

Specific examples of the alkylene carbonate which is a raw material of a urethane compound represented by the general formula (1) include ethylene carbonate, propylene carbonate and the like.

Isocyanate compound

Specific examples of the isocyanate compound which is a raw material of a urethane compound represented by the general formula (1) include 2,5-bis(isocyanatomethyl) bicyclo[2,2,1] heptane or 2,6-bis(isocyanatomethyl)bicyclo [2,2,1] heptane and mixtures thereof, and the like.

Thus obtained various biscarbamate compounds and compounds containing them are novel urethane compounds, and very useful compounds as raw materials of block isocyanate, diisocyanate, developing agent for thermosensible paper, powder paint, and the like.

Polycyclic aliphatic diisocyanate compound

Examples of a polycyclic aliphatic diisocyanate which can be produced by a non-phosgene method using a biscarbamate compound include 2,5-bis(isocyanatomethyl) bicyclo[2,2,1] heptane or 2,6-bis(isocyanatomethyl)bicyclo [2,2,1] heptane and mixtures thereof, and the like.

Production method of polycyclic aliphatic diisocyanate compound

A polycyclic aliphatic diisocyanate compound can be produced without using phosgene by thermallydecomposing a novel urethane compound, namely, a biscarbamate compound having norbornane skeleton. The production of a biscarbamate compound and the production of a polycyclic aliphatic diisocyanate compound by thermaldecomposition of a biscarbamate may be conducted each independently in batch-wise mode or continuous mode. It is preferable that a biscarbamate is synthesized (process I), subsequently the biscarbamate is thermally-decomposed (process II) to produce a polycyclic aliphatic diisocyanate compound.

For producing a biscarbamate having norbornane skeleton, there is preferably used a method in which synthesis is conducted in the co-existence of urea, diamine compound, alcohol, and if necessary, N-unsubstituted carbamate, dialkyl carbonate (hereinafter, referred to as urea method) or a method in which synthesis is conducted using a diamine compound and a carbonate (hereinafter, referred to as carbonate method), from the standpoint of easy availability of raw materials thereof in the reaction of the process I.

(Process I) Urea method

In the process I (urea method), a biscarbamate compound is synthesized by reaction of urea, diamine compound and alcohol as described above. In this synthesis reaction, a N-unsubstituted carbamate and a dialkyl carbonate may be each independently added alone or both of them may be added according to demands.

The molar ratio of respective components in the reaction of the process I is usually diamine:urea:alcohol=1:(2.0 to 2.6):(3 to 10).

The reaction temperature is usually from 80 to 300° C., preferably from 100 to 250° C., particularly preferably from 120 to 240° C.

The reaction pressure is usually from 0.05 MPa to 5 MPa, preferably from 0.08 MPa to 3 MPa, further preferably not more than 2 MPa.

The reaction time is from 4 to 20 hours, preferably from 5 to 10 hours. The production of a biscarbamate compound can be conducted in batch-wise mode or continuous mode, and continuous mode is preferable.

Further, a N-unsubstituted carbamate and a dialkyl carbonate are by-produced by the reaction of urea with alcohol, and these by-products can be separated by distillation and the like from an intended biscarbamate compound, then, recycled as raw materials of the reaction of the process I.

In this process, since ammonia is by-produced in the reaction, the ammonia concentration in the reaction solution is preferably kept at 1 wt. % or less. By thus maintaining the ammonia concentration in the reactor at not more than a certain level, the reaction speed can be accelerated, consequently the reaction time can be shortened, and the selectivity can be increased. For the removal of ammonia from the reaction solution, any method may be used, and examples thereof include the following methods.

1) A method in which a part or all of a reaction solution is drawn out from a reaction vessel, gas-liquid separation is conducted by flush evaporation and the like, and the vapor phase is recycled, after removal of ammonia by distillation, to the reaction vessel.

2) A method in which a vapor phase of a reaction vessel is drawn out, condensed to obtain a condensed solution which is recycled to the reaction vessel, and a non-condensed component is recycled, after removal of ammonia via processes such as distillation, film separation and the like, to the reaction vessel.

3) A method in which a distillation equipment is provided on the upper part of a reaction vessel, and the manufactured apparatus is used as a reaction distillation column as it is for carrying out distillation and separation of ammonia.

The removal of ammonia may be carried out by any of a batch method and a continuous method, and a continuous method is preferable, and as the removal method, the above-described method 2) is preferable.

In this process, a N-unsubstituted carbamate, a dialkyl carbonate and the like are by-produced in addition to ammonia, and a part of them is drawn out from a reaction vessel together with a biscarbamate compound. Though these by-products may be used in the process II without any treatment, usually, separated from a biscarbamate compound by flush evaporation, distillation and the like. These by-products, unreacted raw materials such as alcohol and the like may be recycled to a reaction vessel, or recycled, after purification by distillation and the like, to a reaction vessel.

The present method is suitable particularly in producing a diisocyanate compound having norbornane skeleton.

Raw materials used in this urea method are described below.

Diamine compound

Specific examples of a diamine compound which is a raw material in the present reaction include 2,5-bis(aminomethyl)bicyclo[2,2,1] heptane, 2,6-bis(aminomethyl)bicyclo[2,2,1] heptane and mixtures thereof (hereinafter, abbreviated as NBDA).

Alcohol

As the alcohol used in the urea method, any of the above-described alcohols may be used, and aliphatic primary alcohol is preferable. Examples thereof include methanol, ethanol, propanol, butanol, pentanol, isopentanol and the like, and particularly preferable alcohol is butanol.

(Process I) Carbonate method

In the process I (carbonate method), as described above a biscarbamate compound is synthesized by reaction of a diamine compound and a carbonate. In this synthesis reaction, methyl formate may be added if required, or a diamine compound may be previously reacted with methyl formate to synthesize a bisformamide compound which is further reacted with a carbonate. In the present reaction, a solvent may be used if necessary.

In the carbonate method, it is also possible to use a catalyst. The usable catalyst is a basic substance, namely, an anion exchange resin, alkaline metal and alkaline earth metal alkoxide, and the like, and examples thereof include methoxide, ethoxide and the like of lithium, sodium, potassium, calcium and barium. The basic substance may be used in solid state or in solution state.

The molar ratio of respective components in the reaction of the carbonate method is usually diamine or bisformamide:carbonate=1:(2.0 to 50). The amount used of a catalyst if any is, when sodium methylate is for example used as the catalyst, from 0.01 to 5 wt. %, preferably from 0.1 to 3 wt. % in a reaction crude solution. The reaction temperature is usually from 30 to 200° C., preferably from 50 to 150° C. The reaction pressure is usually from normal pressure to 2 MPa. The reaction time is from 0.1 to 10 hours, preferably from 0.5 to 7 hours.

The production of a biscarbamate compound can be conducted in batch-wise mode or continuous mode, and is preferably conducted in continuous mode.

A biscarbamate crude solution produced in this process can be purified to a required purity by a known method. Particularly when a metal alkoxide is used as a catalyst, the catalyst can be removed by a method in which an anion exchange resin is used or a method in which after neutralization with an acid, de-salting is conducted by washing with water, filtration and the like.

Raw materials used in this carbonate method are described below.

Diamine compound

Specific examples of the diamine compound which is a raw material in the present reaction include 2,5-bis(aminomethyl)bicyclo[2,2,1]heptane, 2,6-bis(aminomethyl)bicyclo[2,2,1] heptane and mixtures thereof (hereinafter, abbreviated as NBDA).

Carbonate

Specific examples of a carbonate used as a raw materials include various carbonates such as dimethyl carbonate, diethyl carbonate, diphenyl carbonate and the like.

Process II

In the process II, a polycyclic aliphatic diisocyanate is produced by thermal-decomposition of a biscarbamate compound having norbornane skeleton. The thermal-decomposition may be conducted without catalyst or using a catalyst, and it is preferable to use a catalyst. The thermal-decomposition may be conducted at one stage, and may also be conducted in multi-divided stages.

In thermal-decomposition of a biscarbamate compound having norbornane skeleton, the content of a biscarbamate compound in a reaction solution is preferably kept at 50 wt. % or less, and further preferably kept at 1 to 30 wt. %. In the thermal-decomposition, a solvent and the like may be contained, and it is preferable that essentially no solvent is contained since solvent purification process can be deleted. Specifically, the total content of compounds having norbornane skeleton in a reaction solution is preferably 60 wt. % or more, further preferably 80 wt. % or more.

Also in the case of continuous thermal-decomposition of a product obtained in the process I, the content of a biscarbamate compound in a reaction solution is preferably kept in the above-described range, namely 50 wt. % or less, in liquid phase of the thermal-decomposition reaction vessel. For controlling the content of a carbamate compound in raw materials within the above-described range, the compound may be diluted with a isocyanate compound and the like, and it is preferable that thermal-decomposition is partially conducted previously. For example, a carbamate compound is thermally-decomposed to be separated into a mixture in which the total content of compounds having a norbornane ring is 60 wt. % or more and the content of a biscarbamate compound is 50 wt. % or less in the thermally-decomposed product, and other components, and the mixture is thermally-decomposed. To keep the concentration of a isocyanate compound low in a thermally-decomposed solution in this procedure is preferable for suppressing production of a compound having high boiling point. Specifically, the total content of isocyanate compounds in a reaction solution which is previously thermally-decomposed is 30 wt. % or less, preferably 20 wt. % or less, particularly preferably 10 wt. % or less.

Figure 7:
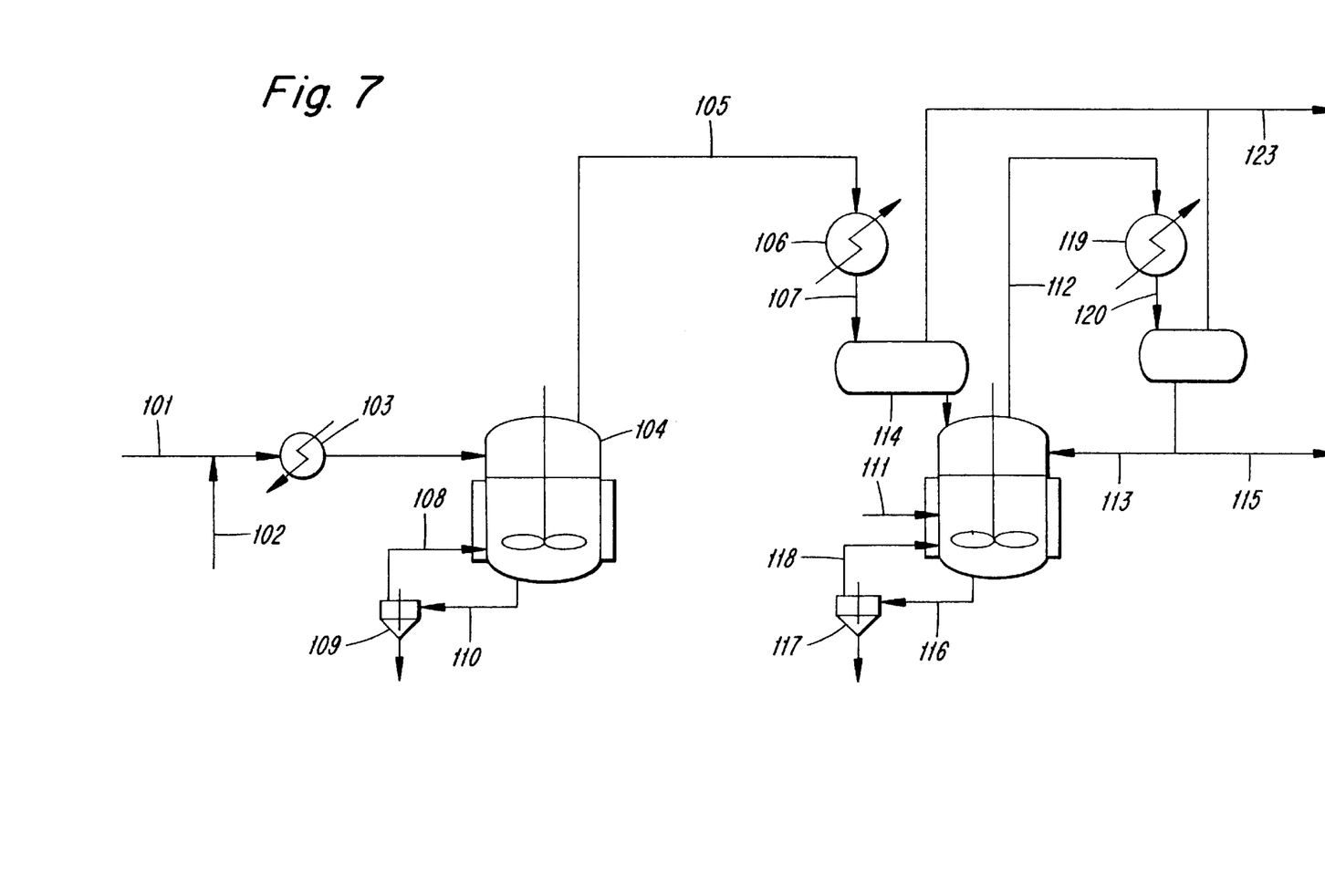
FIG. 7 is a view showing a multi-stage thermal decomposition reaction apparatus.
Figure 8:
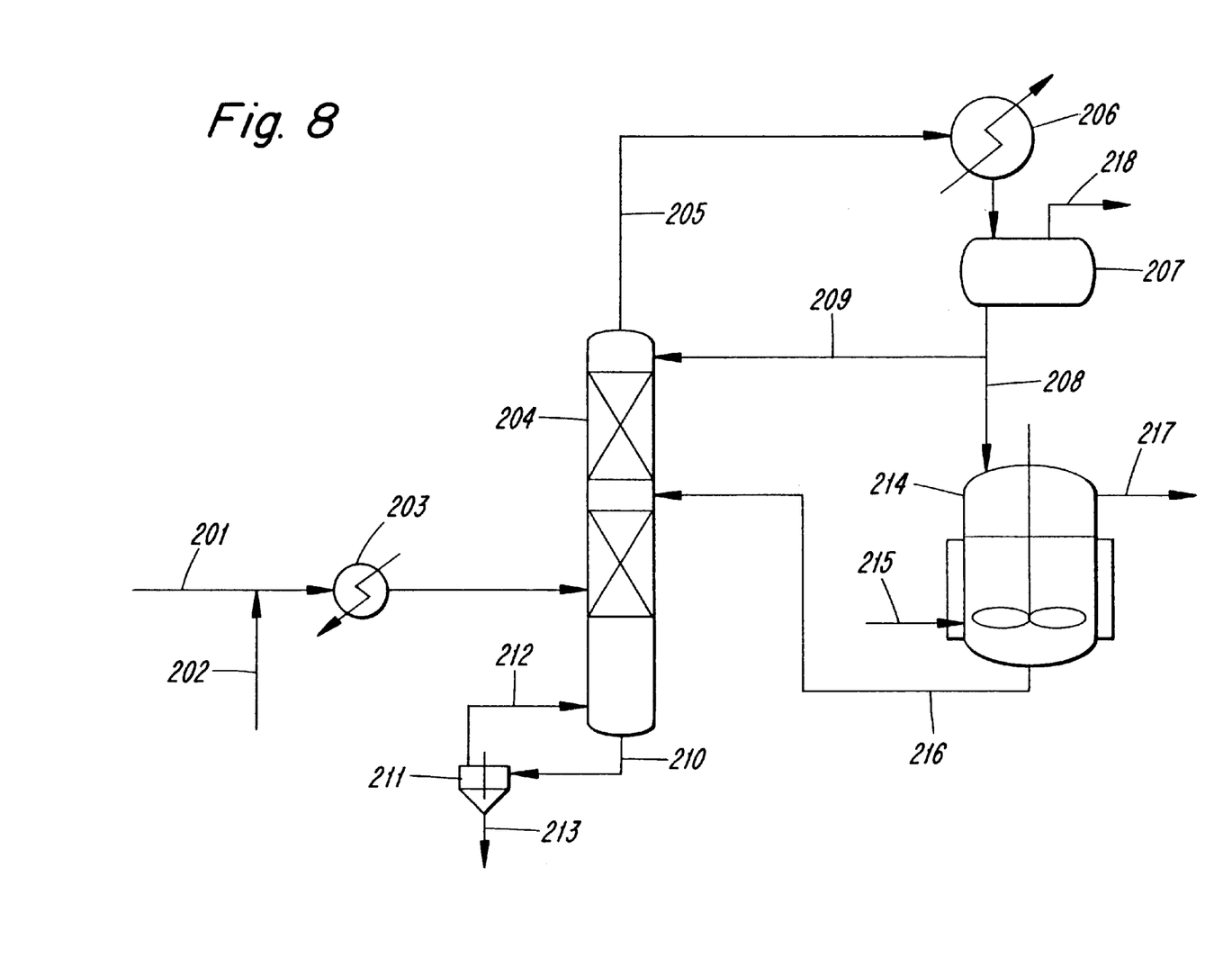
FIG. 8 is a view showing a multi-stage thermal decomposition reaction apparatus using a reaction distillation column.

Examples of apparatuses used in a multi-stage thermal-decomposition reaction method are illustrated in flow sheets shown in FIGS. 7 and 8.

First, a multi-stage thermal-decomposition method in a usual vessel type reaction apparatus is illustrated using FIG. 7.

A biscarbamate is fed together with a catalyst, after heated to given temperature by a pre-heater 103, to a first reaction vessel 104 through a line 101, and thermally-decomposed. Vapor phase containing an isocyanate compound produced in the reaction and alcohol and the like is drawn out through a drawing line 105. Liquid phase is drawn out through a drawing line 110, and separated in a high viscosity type evaporation apparatus 109 into high boiler components such as an oligomer and the like and volatile components, and the volatile components are recycled to the reaction vessel via a line 108. The catalyst is drawn out of the system through lower part of the high viscosity type evaporation apparatus together with the high boiler components (sometimes, referred to as H.B.). The catalyst is fed to the first reaction vessel 104 through a line 102, if required.

The vapor phase drawn out through the line 105 is cooled by a condenser 106, and the condensed liquid is fed to a second reaction vessel 114 and subsequently thermally-decomposed. If necessary, a catalyst is supplied through a line 111. Non-condensed components in the condenser 106 are mainly composed of alcohol, and removed out of the system by a line 123. Vapor phase of the second reaction vessel 114 containing a diisocyanate component produced in the reaction and alcohol is drawn out through a drawing line 112, and cooled in a condenser 119. The condensed liquid is cooled to become a crude polycyclic aliphatic diisocyanate solution. A certain amount of this solution is transferred to purification system through a line 115 to give a purified polycyclic aliphatic diisocyanate, and the remaining part is recycled to the reaction vessel via a line 113. Non-condensed components are composed mainly of alcohol, and drawn out of the system via line 123. Liquid phase of the reaction vessel is drawn out through a line 116, and separated in a high viscosity type evaporation apparatus 117 into high boiler components such as an oligomer and the like and volatile components, and the high boiler components are drawn out of the system through lower part of the high viscosity type evaporation apparatus and the volatile components are recycled to the reaction vessel 114 via a line 118. Depending on occasions, a part or all of liquid phase drawn out through the line 116 may be recycled to the first reaction vessel 104 (not shown). The liquid drawing speed from the lines 110 and 116 is appropriately set so that H.B. can be suitably removed from the reaction system by the high viscosity type evaporation apparatus.

Since alcohol drawn out through the line 123 contains a small amount of a biscarbamate, it is possible that after removal of the alcohol, it is recycled to the first reaction vessel 104 in the process (II). When the process (I) is by a urea method, a drawn solution out of the line 123 can be used without any treatment as raw material alcohol in the process (I).

The thermal-decomposition reaction apparatus may be any of vessel type, tube type and the like, and an apparatus for its temperature control may be appropriately selected from jacket type, external heat exchanger and the like. As the high viscosity type evaporation apparatus, a thin film evaporator and the like are usually listed, however, usual vertical and horizontal heat exchanges may be used providing separation of high boiler components and volatile components is possible.

Then, a multi-stage thermal-decomposition method using a reaction distillation column apparatus will be illustrated using FIG. 8.

A biscarbamate is fed together with a catalyst, after heated to given temperature by a pre-heater 203, to a reaction distillation column 204 through a line 201, and thermally-decomposed. The reaction distillation column 204 has reaction area (area through which a solution containing a catalyst passes), and thermal-decomposition is conducted by passing through this area. The reaction area may have any form providing residence time is maintained during which thermal-decomposition is possible in this area, and for example, a shelf plate, packed bed and the like are used.

Vapor phase is drawn out through a line 205 from the column top part of the reaction distillation column 204. Liquid phase is drawn out through a drawing line 210, and separated in a high viscosity type evaporation apparatus 211 into high boiler components such as an oligomer and the like and volatile components, and the volatile components are recycled to the reaction distillation column via a line 212, and used for boiling.

The catalyst is supplied if necessary through a line 202.

Vapor phase containing an isocyanate component and alcohol by-produced in the reaction and the like is drawn out through a line 205 and cooled in the heat exchanger 206. A condensed liquid condensed in the heat exchanger 206 is kept in a drum 207, non-condensed components composed mainly of alcohol are drawn out of the system through a line 218. The liquid in the drum 207 is supplied in given amount to a second reaction vessel 214 through a line 208, and the remaining part is passed through a line 209 and used as a reflux solution in the reaction distillation column 204. The second reaction vessel is supplied with a new catalyst if necessary through a line 215. Vapor phase drawn out through a line 217 of the second reaction vessel is purified as a crude polycyclic aliphatic diisocyanate in purification system to be a purified polycyclic aliphatic diisocyanate. This crude isocyanate is preferably separated from alcohol by cooling and purified since the content of alcohol in the isocyanate is high. Liquid phase of the second reaction vessel is drawn out through a line 216, and recycled to the reaction distillation column. Regarding recycling position from the second reaction vessel to the reaction distillation column, first reaction equipment, recycling to the nearest composition position in the distillation column is advantageously set depending on liquid composition of the second reaction vessel, and it is preferable to provide a plurality of positions for responding to change in reaction conditions of the second reaction vessel.

It is needless to say that single or a plurality of reaction vessels, purification apparatuses such as a distillation column and the like may be provided between these reaction vessels providing the subject matter of the present invention is not disturbed, and it is not to mention that the technique of the present invention is not restricted to the illustrated apparatus.

The thermal-decomposition temperature of a biscarbamate compound according to the process of the reaction of the process II is, when the thermal-decomposition is carried out in a single stage, usually from 150 to 350° C., preferably from 200 to 300° C. The reaction pressure may advantageously be not more than the vapor pressure of alcohol produced at the above-described reaction temperature, and preferably over the vapor pressure of an isocyanate compound. It is usually from 50 to 760 Torr. The reaction time is usually from 0.1 to 3 hours, though differs depending on conditions. The thermal-decomposition reaction is preferably conducted at a temperature wherein reflux of alcohols is possible without catalyst or in the presence of a catalyst.

Then, the multi-stage reaction will be illustrated.

In the first stage thermal-decomposition, though a solvent and the like may be contained, it is preferable that substantially no solvent is contained, and specifically, the total content of compounds having norbornane skeleton in the reaction solution is preferably 60 wt. % or more, further preferably 80 wt. % or more. When substantially no solvent is contained as the above, the total content of isocyanate compounds in the thermally-decomposition reaction solution is preferably 30 wt. % or less, further preferably 20 wt. % or less, most preferably 10 wt. % or less. By this preference, production of by-products having high boiling points can be suppressed.

As such a method for suppressing the content of isocyanate compounds in a reaction solution, there are a method in which vapor phase in the reactor is drawn out sequentially and the like.

As other method for suppressing production of by-products having high boiling points, there is a method in which the content of a biscarbamate compound in a reaction solution is suppressed. In this case, the content of a biscarbamate compound in a reaction solution is preferably 50 wt. % or less, further preferably 30 wt. % or less. As a method for keeping the content of a biscarbamate at not more than the above-described value and carrying out thermal-decomposition, there is for example listed a method in which dilution with an isocyanate compound and the like is conducted.

As such a method for suppressing production of components having high boiling points, any of the above-described methods may be used alone or in combination. When treatment is conducted continuously from the process I, it is preferable to control the content of an isocyanate compound.

In the case of thermal-decomposition in two stages, the reaction temperature in the first reaction vessel is usually from 150 to 350° C., preferably from 200 to 300° C. The reaction pressure is not more than the vapor pressure of an isocyanate compound at the above-described reaction temperature, and usually from 1 to 500 Torr. The reaction time is usually from 0.1 to 3 hours, though varies depending on conditions. The thermal-decomposition reaction is preferably conducted at a temperature wherein an isocyanate compound can be refluxed without catalyst or in the presence of a catalyst. An isocyanate compound and alcohol produced in the reaction are drawn in the form of vapors out of a reaction vessel, separated by condensation and the like, and components composed mainly of alcohol are drawn out of the system and components composed mainly of an isocyanate may be fed to a second reaction vessel as crude products without any treatment or may be purified before feeding to a second reaction vessel. The crude products are mainly composed of a monoisocyanate monocarbamate, and contain also a biscarbamate compound and a diisocyanate compound.

An isocyanate obtained in the first reaction vessel is introduced into the second reaction vessel operated at a temperature at least 5° C. higher than that of the first reaction vessel. The reaction pressure is a pressure wherein a diisocyanate compound can be vaporized at the reaction temperature, and usually from 1 to 500 Torr. It is important that the content of a biscarbamate compound in a reaction solution composed of a compound having norbornane skeleton in the heating part of the second reaction vessel is at least not more than 50 wt. %, preferably not more than 30 wt. %.

A diisocyanate compound and alcohol are drawn in the form of vapors out of the second reaction vessel, and separated into a diisocyanate condensed liquid and an alcohol condensed liquid by fractional condensation.

The diisocyanate condensed liquid can be distilled and purified to give a diisocyanate compound having high purity, if required.

The alcohol condensed liquids obtained from both of the first and second reaction vessels contain a small amount of a biscarbamate compound, and it can be recycled, for example, to synthesis process of a biscarbamate compound.

Biscarbamate compound used in thermal-decomposition reaction

The biscarbamate compound used as a raw material for thermal-decomposition in the process II may be any biscarbamate compound providing it is a desired biscarbamate compound represented by the general formula (1) corresponding to a polycyclic aliphatic diisocyanate having norbornane skeleton.

It is preferable that a compound obtained in the process I is continuously allowed to react.

The reaction solution from the process I is not restricted providing it contains a biscarbamate compound, and the content of a biscarbamate compound is preferably 85 wt. % or more, further preferably 90 wt. % or more.

Catalyst for thermal-decomposition reaction

As the catalyst used in thermal-decomposition reaction of the invention according to the instant application, there is used a metal compound of an element belonging to IB, IIB, IIIA, IVA, IVB, VA, VB, VIA, VIIA and VIII group of the periodic table, for example, a metal compound of an element such as Cu, Zn, Al, Sn, Ti, V, Fe, Co, Ni and the like. In the above-described metal compounds, a halide or oxide is suitable, and particularly, chloride and oxide of zinc are preferable.

When thermal-decomposition is conducted in multi stages, catalysts may be used if necessary in thermal-decomposition reactions in the first and second reaction vessels, and different catalysts may be respectively used in the respective reaction stages, though the same catalyst is preferably used.

The thermal-decomposition reaction may be carried out in any of batch-wise mode and continuous mode, and continuous mode is preferable.

The following examples further illustrate the present invention specifically, but do not limit the scope of the present invention.

EXAMPLE 1

Synthesis of Mixture of 2,5-bis (methoxycarbonylaminomethyl)-bicyclo[2,2,1] heptane and 2,6-bis(methoxycarbonylaminomethyl)-bicyclo[2,2,1] heptane 100 g of dehydrated methyl alcohol was charged in a dried flask, 110 g of a mixture of 2,5-bis(isocyanatomethyl)-bicyclo[2,2,1] heptane and 2,6-bis(isocyanatomethyl)-bicyclo[2,2,1] heptane was added dropwise over a period of 30 minutes under reflux while stirring, then, they were reacted for 4 hours under reflux of methanol.

Methyl alcohol was removed from the reaction solution under reduced pressure to obtain 130 g of oily substance. The element analysis values of the resulted compound are as follows.

| Element Analysis Values (%) (for $C_{13}H_{22}N_2O_4$) | | |
| --- | --- | --- |
| C | H | N |
| Calc.: 57.76 | 8.20 | 10.36 |
| Found: 57.73 | 8.15 | 10.31 |

Figure 1:
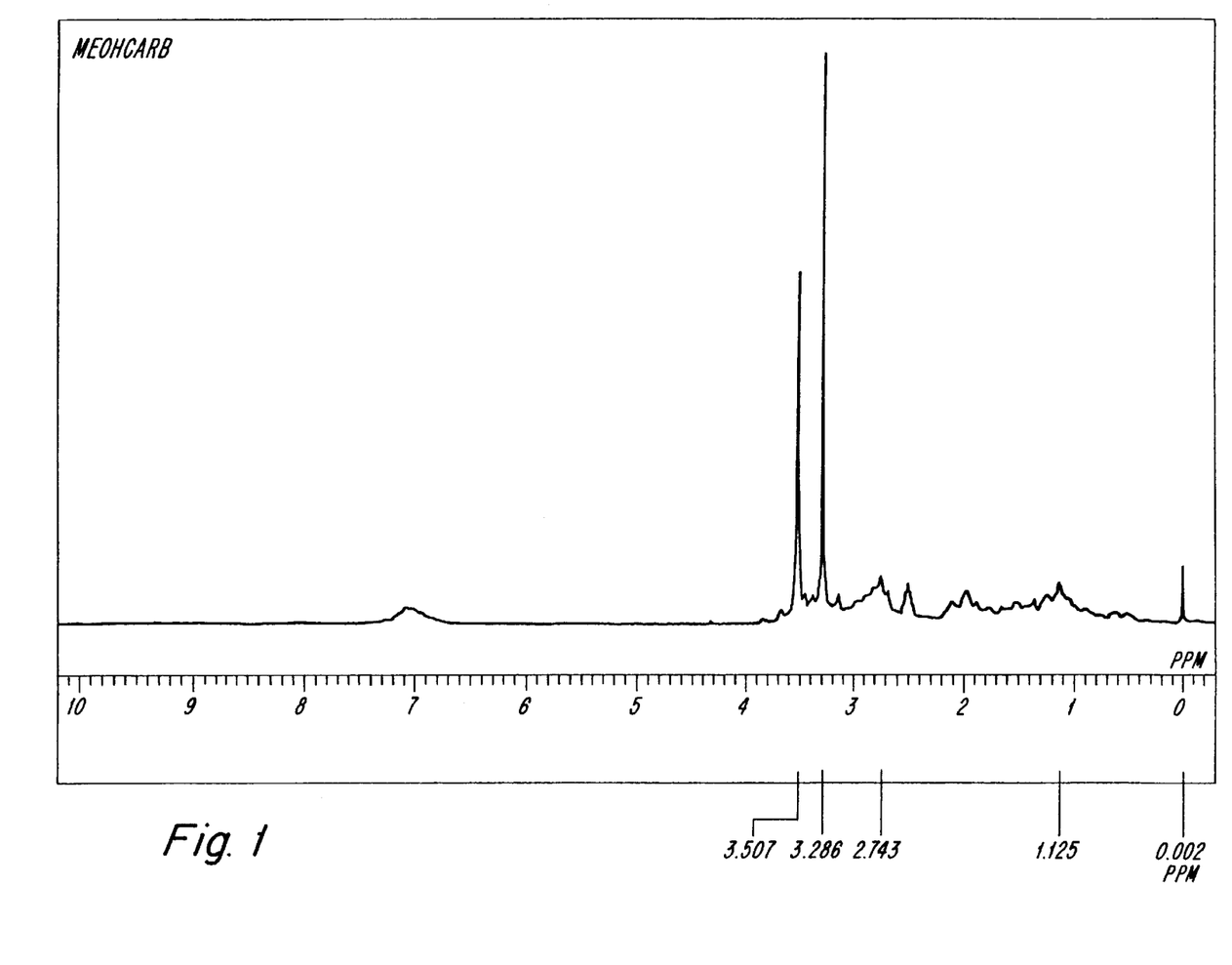
FIG. 1 shows proton NMR spectrum of a compound obtained in Example 1.
Figure 2:
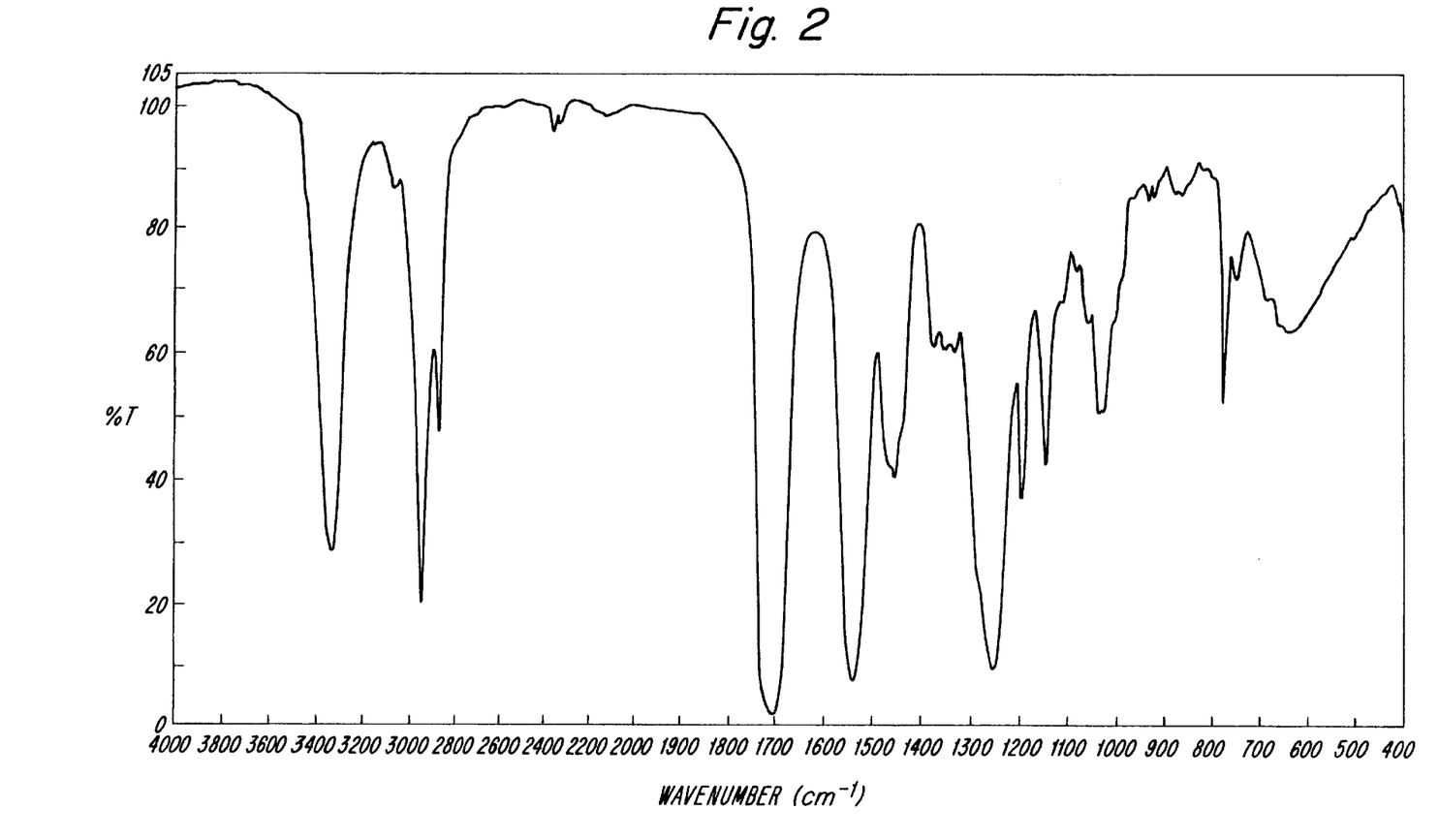
FIG. 2 shows IR spectrum of a compound obtained in Example 1.

The proton NMR of this compound is shown in FIG. 1 and the IR spectrum of this compound is shown in FIG. 2. In MS spectrum, (M+)=270 was observed.

From the above-described results, this compound was identified as a mixture of 2,5-bis(methoxycarbonylaminomethyl)-bicyclo[2,2,1] heptane and 2,6-bis(methoxycarbonylaminomethyl)-bicyclo[2,2,1] heptane.

EXAMPLE 2

Synthesis of Mixture of 2,5-bis(butoxycarbonylaminomethyl)-bicyclo[2,2,1] heptane and 2,6-bis(butoxycarbonylaminomethyl)-bicyclo[2,2,1] heptane 180 g of dehydrated n-butyl alcohol was charged in a dried flask, heated to 80° C., and 80 g of a mixture of 2,5-bis(isocyanatomethyl)-bicyclo[2,2,1] heptane and 2,6-bis(isocyanatomethyl)-bicyclo[2,2,1] heptane was added dropwise over a period of 30 minutes while stirring. They were reacted for 4 hours at 80° C. while stirring, then, n-butyl alcohol was removed from the reaction solution under reduced pressure to obtain 120 g of oily substance. The element analysis values of the resulted compound are as follows.

| Element Analysis Values (%) (for $C_{19}H_{34}N_2O_4$) | | |
| --- | --- | --- |
| C | H | N |
| Calc.: 64.38 | 9.67 | 7.90 |
| Found: 64.55 | 9.63 | 7.93 |

Figure 3:
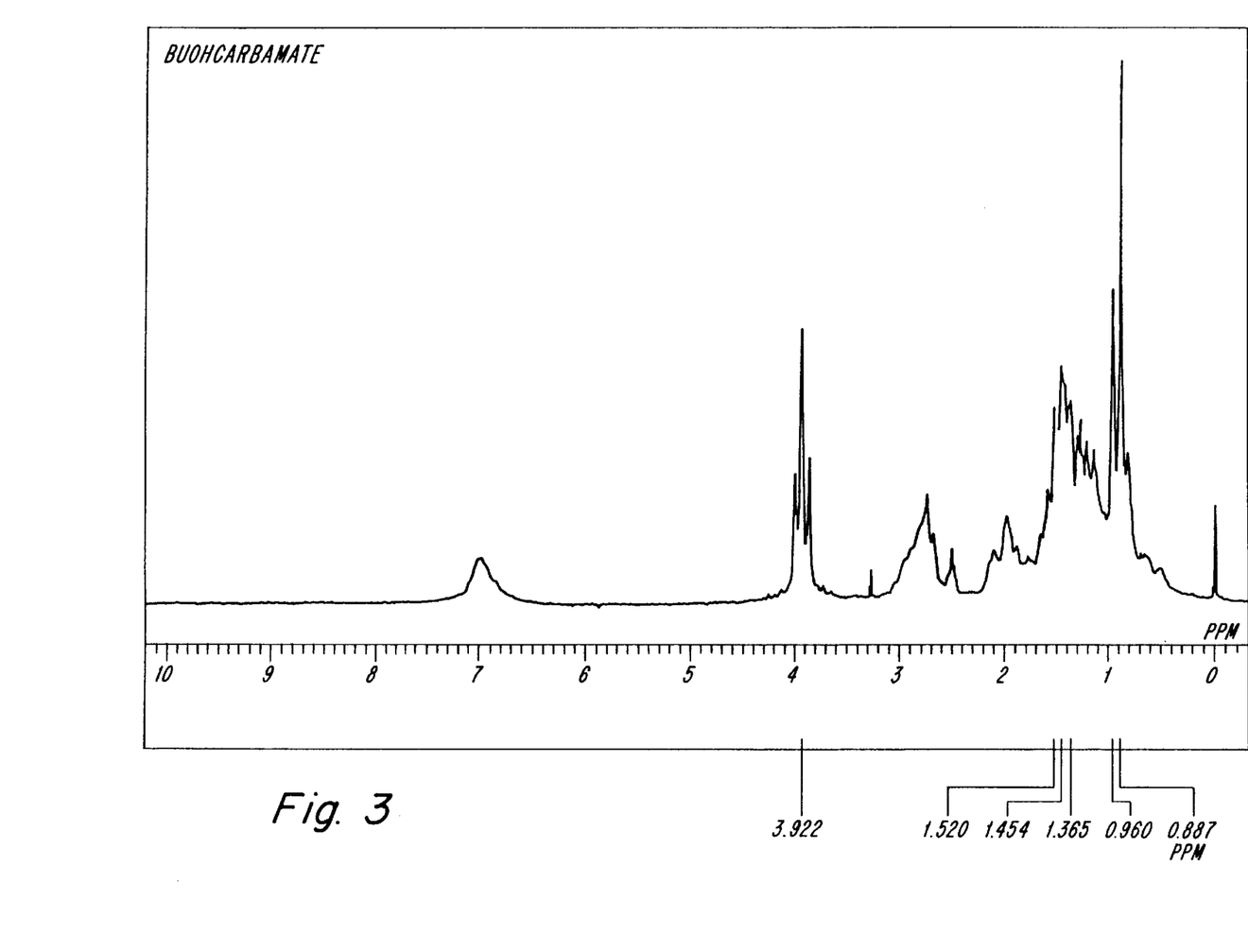
FIG. 3 shows proton NMR spectrum of a compound obtained in Example 2.
Figure 4:
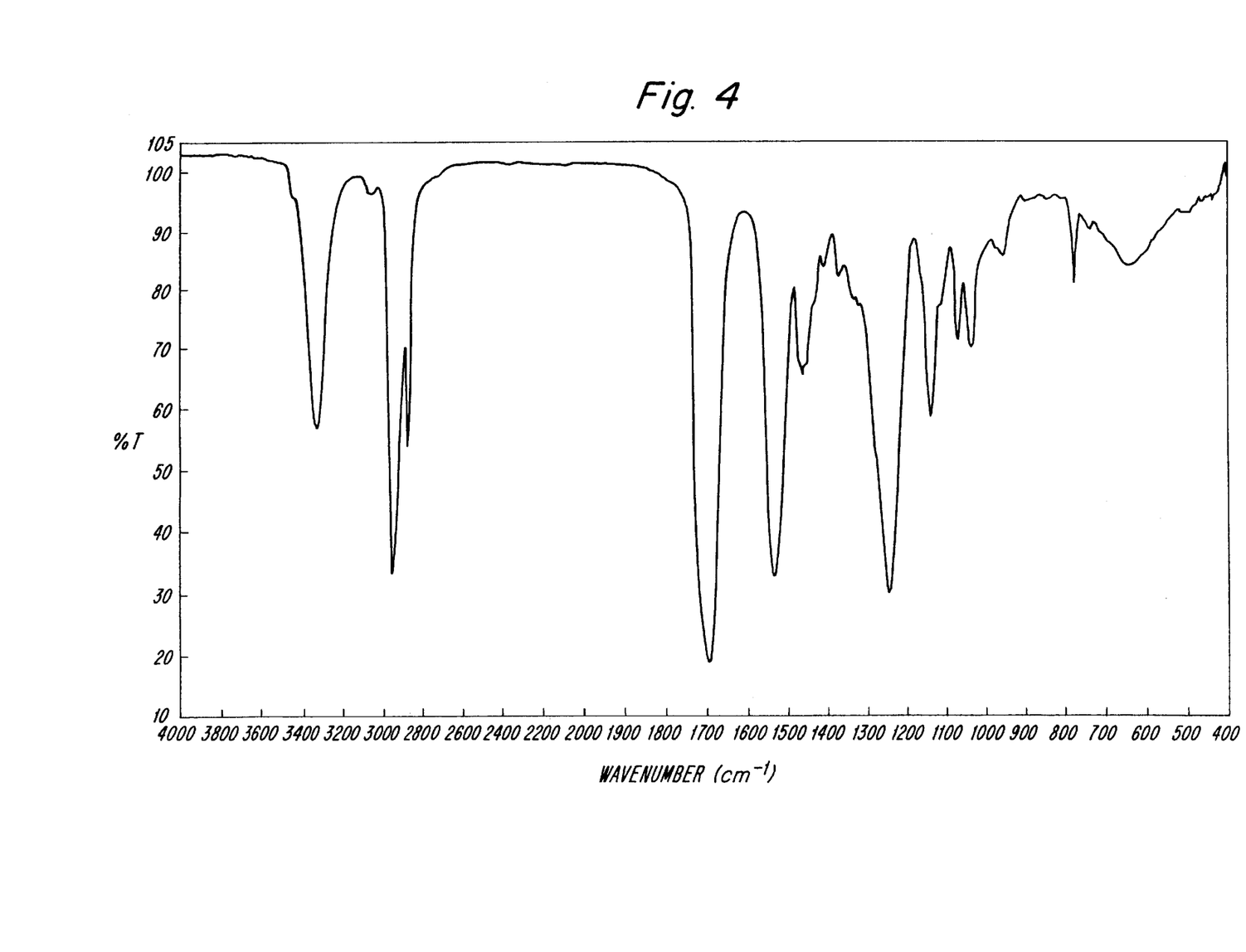
FIG. 4 shows IR spectrum of a compound obtained in Example 2.

The proton NMR of this compound is shown in FIG. 3 and the IR spectrum of this compound is shown in FIG. 4. In MS spectrum, (M+)=354 was observed.

From the above-described results, this compound was identified as a mixture of 2,5-bis(butoxycarbonylaminomethyl)-bicyclo[2,2,1] heptane and 2,6-bis(butoxycarbonylaminomethyl)-bicyclo[2,2,1] heptane.

EXAMPLE 3

Synthesis of Mixture of 2,5-bis(phenoxycarbonylaminomethyl)-bicyclo[2,2,1] heptane and 2,6-bis(phenoxycarbonylaminomethyl)-bicyclo[2,2,1] heptane 200 g of dehydrated phenol was charged in a dried flask, heated to 80° C., and 80 g of a mixture of 2,5-bisisocyanatomethyl-bicyclo[2,2,1] heptane and 2,6-bisisocyanatomethyl-bicyclo[2,2,1] heptane was added dropwise over a period of 30 minutes while stirring. They were reacted for 4 hours at 80° C. while stirring, then, phenol was removed from the reaction solution under reduced pressure to obtain 125 g of a white solid (m.p.: 156° C.).

| Element Analysis Values (%) (for $C_{23}H_{26}N_2O_4$) | | |
| --- | --- | --- |
| C | H | N |
| Calc.: 70.03 | 6.64 | 7.10 |
| Found: 70.10 | 6.69 | 7.02 |

Figure 5:
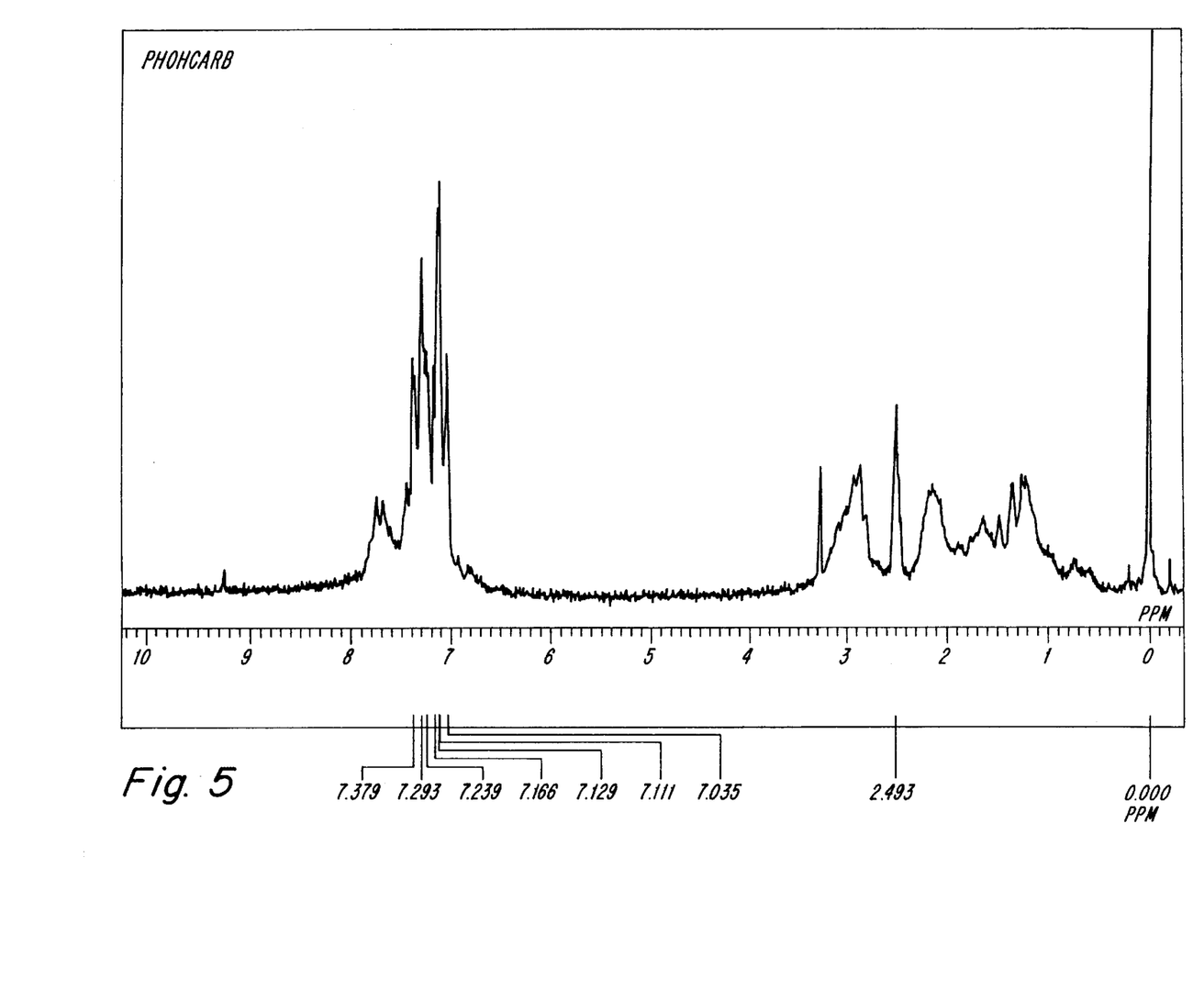
FIG. 5 shows proton NMR spectrum of a compound obtained in Example 3.
Figure 6:
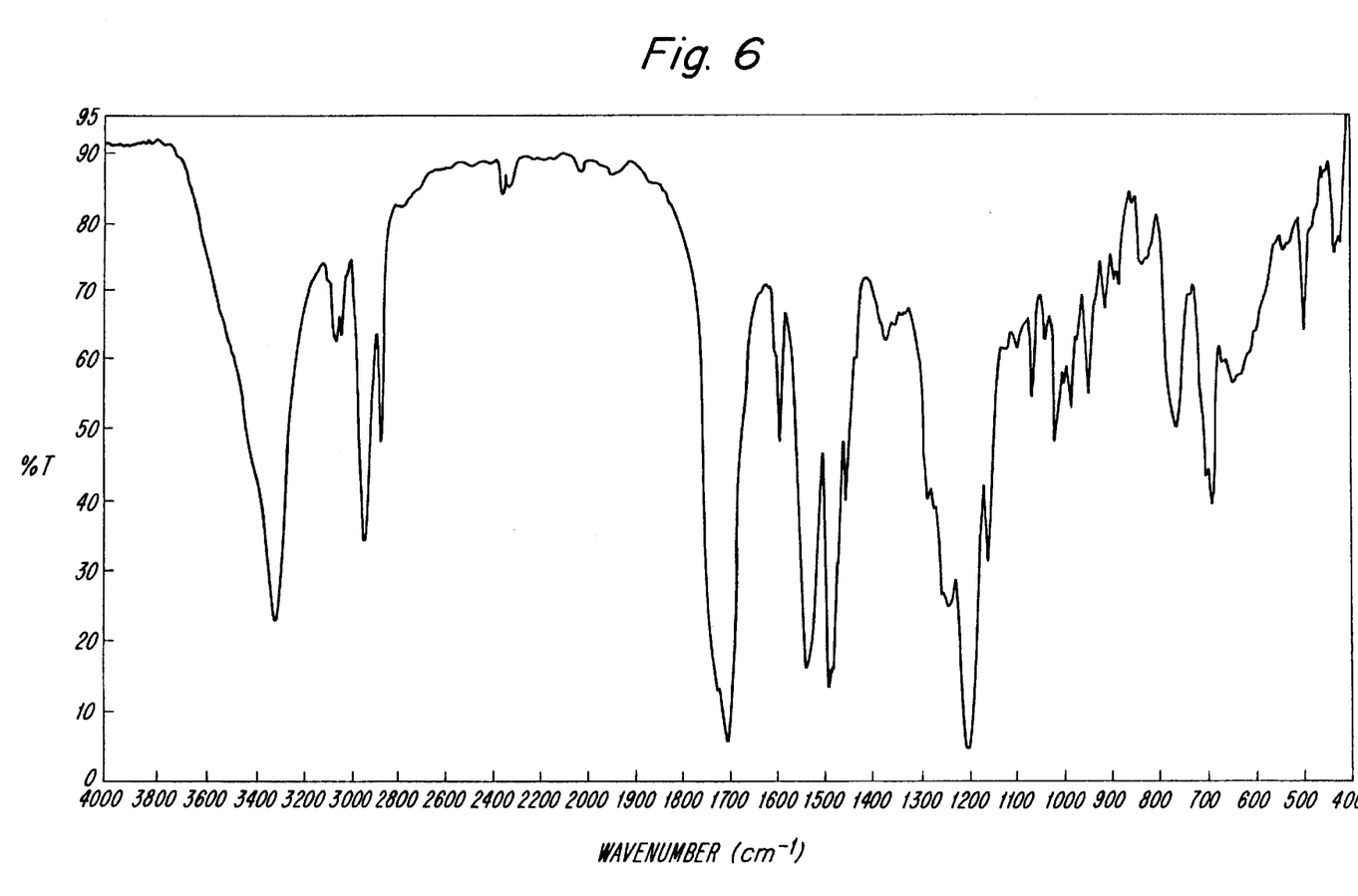
FIG. 6 shows IR spectrum of a compound obtained in Example 3.

The proton NMR of this compound is shown in FIG. 5 and the IR spectrum of this compound is shown in FIG. 6. In MS spectrum, (M+)=394 was observed.

From the above-described results, this compound was identified as a mixture of 2,5-bis(phenoxycarbonylaminomethyl)-bicyclo[2,2,1] heptane and 2,6-bis(phenoxycarbonylaminomethyl)-bicyclo[2,2,1] heptane.

EXAMPLE 4

Synthesis of Mixture of 2,5-bis(butoxycarbonylaminomethyl)-bicyclo[2,2,1] heptane and 2,6-bis(butoxycarbonylaminomethyl)-bicyclo[2,2,1] heptane A 100 cc autoclave equipped with an electromagnetic stirrer, thermocouple protecting tube, pressure meter, pressure control valve, condenser and liquid transporting pump was used as a reaction vessel. In the autoclave was charged 10.8 g of NBDA, 10.0 g of urea and 30.7 g of n-butanol, and sealed. The reaction vessel was placed in an electric furnace, and purged with a nitrogen gas, then, pressurized at 1.5 MPa, and reaction was initiated while stirring and heating. During the reaction, the pressure control valve was operated to maintain the temperature in the reaction vessel at 235° C. A vapor drawn out through the pressure control valve was introduced into the condenser, and n-butanol was condensed and recovered. n-Butanol of the same amount as the recovered amount was fed by the pump into the reaction vessel while reacting for 6 hours. The concentration of ammonia in the reaction solution was 0.5% or less throughout the reaction time.

After cooling, the reaction solution was recovered and analyzed by liquid chromatography to find that the solution contained 24.1 g of a mixture of 2,5-bis(butoxycarbonylaminomethyl)-bicyclo[2,2,1] heptane and 2,6-bis(butoxycarbonylaminomethyl)-bicyclo[2,2,1] heptane (hereinafter, abbreviated as NBBC) (yield: 97.7% based on NBDA).

EXAMPLE 8

Synthesis of NBBC

The synthesis of NBBC described in Example 4 was carried out in the same reaction conditions except that the amount vaporized of n-butanol was reduced. The concentration of ammonia in the reaction solution during the reaction was 1.2 wt. % or more.

After cooling, the reaction solution was recovered and analyzed by liquid chromatography to find production of 18.7 g of NBBC (yield: 75.6% based on NBDA) and to detect a polyurea compound.

EXAMPLE 5

Thermal-decomposition Experiment of NBBC: First Reaction

A 100 cc glass flask equipped with a stirrer, thermocouple, pressure meter, isocyanate condenser, isocyanate receiver, butanol trap and vacuum pump was used as a reaction vessel. In the flask was charged 40 g of NBBC, and zinc chloride was added so that the concentration was 200 ppm based on NBBC. The pressure was controlled to 10 Torr, and the temperature of the gas outlet part of the flask was maintained at 210° C. The temperature of the isocyanate condenser was set at 90° C. The reaction vessel was immersed in an oil bath, and the time when the temperature of the content of the reaction vessel reached 230° C. was regarded as reaction initiation point. The temperature of the content of the reaction vessel was 235° C.

40 minutes after the reaction initiation, 0.9 g of liquid remained in the reaction vessel. There remained 28.7 g of liquid condensed in the isocyanate receiver, and contained 5.2 g of NBBC 18.1 g of a monoisocyanate monocarbamate (hereinafter, abbreviated as NBMI) and 5.4 g of norbornane diisocyanate (hereinafter, abbreviated as NBDI). Liquid recovered from the butanol trap was a mixture of 1.6 g of NBBC and 8.7 g of n-butanol. The total yield of the distilled NBBC, NBMI and NBDI was 97.5%.

<Thermal-decomposition reaction of NBMI: Second reaction>

25 g of the liquid in the isocyanate receiver obtained in the first reaction was charged in the same reaction apparatus as in the first reaction, and zinc chloride was added so that the concentration was 200 ppm based on the content of the reaction vessel. The pressure was controlled to 20 Torr, and the temperature of the gas outlet part of the flask was maintained at 210° C. The temperature of the isocyanate condenser was set at 120° C. The reaction vessel was immersed in an oil bath, and the time when the temperature of the content of the reaction vessel reached 250° C. was regarded as reaction initiation point. The temperature of the content of the reaction vessel was 253° C.

40 minutes after the reaction initiation, 0.8 g of liquid remained in the reaction vessel. The liquid condensed in the isocyanate receiver contained 0.8 g of NBMI and 17.4 g of NBDI, and NBBC was not detected. Liquid in the butanol trap was a mixture of 0.6 g of NBBC and 5.4 g of n-butanol. The total yield of the distilled NBBC, NBMI and NBDI was 97% based on the charging amount into the second reaction vessel. Accordingly, the total yield of NBBC, NBMI and NBDI in the first reaction and the second reaction was calculated as 94.6%.

EXAMPLE 9

Thermal-decomposition of Monoisocyanate Compound is Carried Out at the Same Temperature as in First Reaction Vessel The same experiment as in the second reaction in Example 5 was conducted except that only the reaction temperature was changed to 235° C. 40 minutes later, 20.5 g of highly viscous liquid of which quantitative determination was impossible remained in the reaction vessel. In the isocyanate receiver, 4.4 g of liquid composed of 4.2 g of NBDI and 0.2 g of NBMI was recovered. n-Butanol was not recovered in the butanol trap. The total yield of the distilled NBMI and NBDI was 21% based on the charging amount into the second reaction vessel.

EXAMPLE 6

Synthesis of Mixture of 2,5-bis (methoxycarbonylaminomethyl)-bicyclo[2,2,1] heptane and 2,6-bis(methoxycarbonylaminomethyl)-bicyclo[2,2,1] heptane A 300 cc flask equipped with a stirrer, thermometer, dropping funnel and condenser was used as a reaction vessel. Under nitrogen flow, 34.8 g of dimethyl carbonate, and 1.1 g of a 28% methanol solution of sodium methoxide were added into the flask, and 18.7 g of methanol was added and the mixture was heated to the reflux temperature (65° C.). From the dropping funnel, 14.2 g of NBDA was added dropwise over a period of 10 minutes, and the mixture was further heated for 3 hours. After cooling, the crude reaction solution was recovered and analyzed by liquid chromatography to find that the solution contained 24.2 g of a mixture of 2,5-bis(methoxycarbonylaminomethyl)-bicyclo[2,2,1] heptane and 2,6-bis(methoxycarbonylaminomethyl)-bicyclo [2,2,1] heptane (yield: 97.2% based on NBDA).

EXAMPLE 7

Synthesis of Mixture of 2,5-bis (phenoxycarbonylaminomethyl)-bicyclo[2,2,1] heptane and 2,6-bis(phenoxycarbonylaminomethyl)-bicyclo[2,2,1] heptane

A 300 cc flask equipped with a stirrer, thermometer, dropping funnel and condenser was used as a reaction vessel. Under nitrogen flow, 82.9 g of diphenyl carbonate was charged into the flask, and the mixture was heated to 95° C. From the dropping funnel, 14.8 g of NBDA was added dropwise over a period of 1 hour, and the mixture was further heated for 2 hours. After cooling, the crude reaction solution was recovered and analyzed by liquid chromatography to find that the solution contained 28.4 g of a mixture of 2,5-bis(phenoxycarbonylaminomethyl)-bicyclo[2,2,1] heptane and 2,6-bis(phenoxycarbonylaminomethyl)-bicyclo [2,2,1] heptane (yield: 74.8% based on NBDA).

The compound obtained in the present invention is a novel urethane compound, and very useful as a raw material in various uses such as block isocyanate, diisocyanate, developing agent for thermosensible paper, powder paint and the like.

Further, according to the present method, a polycyclic aliphatic diisocyanate compound can be produced in high yield economically using a diamine compound, urea and alcohol as raw materials. Namely, in synthesizing a biscarbamate compound from a diamine compound having norbornane skeleton, urea and alcohol by the method of the present invention, the reaction speed and the reaction selectivity can be increased by controlling ammonia concentration in the reaction solution to not more than 1 wt. %, and in thermally-decomposing the biscarbamate, by conducting the thermal-decomposition in two-stage procedure under non-solvent condition, production of by-products having high boiling points can be significantly suppressed and a diisocyanate compound can be produced in high yield.

What is claimed is:

1. A biscarbamate represented by the following general formula (1):

(1)

(wherein, R1 and R2 may be the same or different and represent a straight or branched alkyl group, (substituted) cycloalkyl group or (substituted) aryl group.).

2. A novel urethane compound comprising a biscarbamate described in claim 1.

3. A method for producing a biscarbamate compound wherein a biscarbamate compound described in claim 1 is produced from urea or carbonate.

4. A method for producing a biscarbamate compound wherein in producing a biscarbamate compound described in claim 1 using a diamine compound, urea and aliphatic alcohol, the production is conducted while removing out of the reaction system ammonia by-produced in reaction of the diamine compound, urea and aliphatic alcohol.

5. The method for producing a biscarbamate compound according to claim 4, wherein vapor phase is drawn out from a reaction vessel and is condensed, then, a condensed component is recycled to the reaction vessel, and a non-condensed component is also recycled to the reaction vessel after removal of ammonia therefrom.

6. The method for producing a biscarbamate compound according to claim 4, wherein the production is conducted while maintaining the ammonia concentration in the reaction solution at 1 wt. % or less.

7. A method for producing a polycyclic aliphatic diisocyanate wherein a cyclic diisocyanate is produced by thermally-decomposing a biscarbamate described in claim 1.

8. The method for producing a polycyclic aliphatic diisocyanate according to claim 7, wherein the thermal-decomposition is conducted at a total content of compounds having a norbornane ring in the thermal-decomposition reaction solution of 60 wt. % or more and a content of a biscarbamate in the thermal-decomposition reaction solution of 50 wt. % or less.

9. The method for producing a polycyclic aliphatic diisocyanate according to claim 7, wherein a biscarbamate is thermally-decomposed, the thermally-decomposed product is separated into a mixture in which the total content of compounds having a norbornane ring is 60 wt. % or more and the content of a biscarbamate is 50 wt. % or less, and other components, and the mixture is thermally-decomposed to produce a polycyclic aliphatic diisocyanate.

10. The method for producing a polycyclic aliphatic diisocyanate according to claim 7, wherein the thermal-decomposition reaction is conducted at least at two stages, and thermal-decomposition of the latter stage is conducted at a temperature at least 5° C. higher than that of thermal-decomposition of the former stage.

* * * * *